(12) United States Patent
Sheehan

(10) Patent No.: US 9,889,037 B2
(45) Date of Patent: Feb. 13, 2018

(54) SPINAL TRACTION DEVICE AND METHOD OF USE

(71) Applicant: Kelly Sheehan, Minnetonka, MN (US)

(72) Inventor: Kelly Sheehan, Minnetonka, MN (US)

(*) Notice: Subject to any disclaimer, the term of this patent is extended or adjusted under 35 U.S.C. 154(b) by 220 days.

(21) Appl. No.: 14/571,934

(22) Filed: Dec. 16, 2014

(65) Prior Publication Data

US 2015/0164674 A1    Jun. 18, 2015

Related U.S. Application Data

(60) Provisional application No. 61/916,625, filed on Dec. 16, 2013.

(51) Int. Cl.
| | | |
|---|---|---|
| *A61F 5/048* | (2006.01) | |
| *A61H 1/02* | (2006.01) | |
| *A61G 7/07* | (2006.01) | |
| *A61G 13/12* | (2006.01) | |
| *A61G 15/12* | (2006.01) | |

(52) U.S. Cl.
CPC .......... *A61F 5/048* (2013.01); *A61H 1/0218* (2013.01); *A61H 1/0222* (2013.01); *A61H 1/0292* (2013.01); *A61H 1/0296* (2013.01); *A61G 7/07* (2013.01); *A61G 7/072* (2013.01); *A61G 13/121* (2013.01); *A61G 15/125* (2013.01)

(58) Field of Classification Search
CPC .. A61G 1/0293; A61G 1/0212; A61G 1/0225; A61G 1/0231; A61G 1/0287; A61G 13/105; A61G 1/013; A61G 2210/30; A61G 2220/10; A61G 13/121; A61G 2200/325; A61G 13/12; A61G 13/1245; A61G 7/07; A61G 7/072; A61G 15/125; A61F 5/048; A61F 5/05883; A61H 1/0218; A61H 1/0222; A61H 1/0292; A61H 1/0296
USPC .................. 602/32–39; 128/870; 5/622, 636; 297/220, 238.4, 391, 283.4
See application file for complete search history.

(56) References Cited

U.S. PATENT DOCUMENTS

| | | | | |
|---|---|---|---|---|
| 4,033,339 A | * | 7/1977 | Roberts | A61F 5/055 5/622 |
| 4,144,880 A | * | 3/1979 | Daniels | A61H 1/0292 606/242 |
| 4,863,218 A | * | 9/1989 | McCrackin | A61G 15/125 297/391 |
| 5,192,306 A | * | 3/1993 | Scott | A61G 13/009 5/608 |
| 7,846,080 B2 | * | 12/2010 | Boren | A61H 1/0218 482/130 |

\* cited by examiner

*Primary Examiner* — Keri J Nelson
(74) *Attorney, Agent, or Firm* — Gutwein Law; Greg N. Geiser

(57) ABSTRACT

A cervical spine traction device and method of use to apply a controlled tractional force to the cervical spine of a patient to remodel and correct improper spinal positioning. The device is affixed to an end of a table and includes a mounting plate, a riser, a height adjusting means, an angular adjusting means, a tensioning means, and a headrest. The patient is placed into the device in a prone position and a tractional force is applied to cervical spine of the patient to remodel proper spinal positioning.

8 Claims, 5 Drawing Sheets

SPINAL TRACTION DEVICE AND METHOD OF USE

CROSS REFERENCE TO RELATED APPLICATIONS

This application claims priority to U.S. Provisional Patent Application No. 61/916,625 filed 16 Dec. 2013 to the above named inventor, and is herein incorporated by reference in its entirety.

FEDERALLY SPONSORED RESEARCH

Not Applicable

SEQUENCE LISTING OR PROGRAM

Not Applicable

FIELD OF THE INVENTION

The present invention relates to a spinal traction device and method for use.

BACKGROUND OF THE INVENTION

The below disclosed invention relates generally to a device and method to apply traction forces to the neck of a user to improve and remodel proper whole spinal posture. The human spine is comprised of three distinct curved regions: the cervical (neck), the thoracic (back), and lumbar (lower back). Each of these regions is composed of individual bones called vertebrae. These vertebrae are essentially aligned in an interlocking fashion and supported between each independently by an intervertebral disc. When viewed laterally the vertebrae and discs form a continuous spinal column extending from the head to the tailbone. This spinal column is curved to aid in weight bearing, strength, movement, and support the daily activities of a typical human.

A proper curvature of the spine is extremely important in an individuals overall health and well being. Improper alignment or curvature can result in constant pain and lead to additional health problems. One method of correcting improper positioning of the spine is through traction. Traction, as it used in this specification, is the application of force in a specific direction to the anatomy of a patient for the purposes of remodeling or realigning impacted joints or structures. Repeated traction to an affected area can remodel the patient's muscle, bones, tendons, etc. by improving the elasticity and strength of the surrounding supportive soft and connective tissues.

One particular problem affecting several individuals is cervical kyphosis or reverse lordosis of the cervical spine. A normal lordosis of the of the cervical spine will from a lateral view look like a wide "C." This lordotic curve of the cervical spine helps to support the head and spine of the user and even offers cushioning in the event of an impact. If this curve is too deep or too straight, problems can develop.

Current traction devices in the market are large and focused on the larger regions of the spine and not the cervical spine. Therefore, there is a treatment need for a device that takes up a small amount of space and that can easily be used to apply traction to the cervical spine of a patient to aid the remodeling and realignment of a patients cervical spine. Preferably this device is easy to use, easily adjustable, and adaptable to existing equipment.

SUMMARY OF THE INVENTION

The present invention provides a device and method to apply safe and consistent traction to the cervical spine of a patient. The device is affixed to an end of a treatment table and allows for the placement of a patients head onto a support strap while the patient is in a lying position. The device is then adjusted to provide the proper angle for treatment and traction is applied to the patient's cervical spine area. The placement and traction position of the device allows for a specific global head to the ribs downward and forward pull on the cervical misaligned spinal unit to lordotic fashion. The device provides the possibility for translation, extension, and compression of the cervical spinal area.

In particular, the device includes a mounting plate having a top end and a bottom end with the distance between the top end and the bottom end extending a height. The mounting plate is attached to an end of a treatment table and aligned with a potential patient's head when the patient is lying on the table in a prone position. The bottom end includes a foot for resting on a surface and offering support. The foot includes a tab, the tab sized for receipt of a first end of a height adjusting means. The mounting plate includes a pair of mounting brackets centrally located on each side of the mounting plate, the mounting brackets extending perpendicular to the mounting plate and opposite the table.

The mounting brackets are sized and shaped to receive a tensioning means that is designed to provide tension to the neck of the patient. In the preferred embodiment the tensioning means is a rope having a pair of ends with a first end affixed to one of the pair of mounting brackets that extends around the device and over the patients neck. The rope second end is secured to the second mounting bracket with a cleat. Preferably, the cleat is a standard cam action cleat that allows for quick and secure adjustment.

A riser is slidably received along the height of the mounting bracket. The riser having a free end and an attachment end opposite the free end. The attachment end extends from the riser height and has a bifurcation. The bifurcation culminating in a pair of attachment loops. The riser includes a pair of tabs to receive a second end of the height adjusting means. Wherein adjustment of the height adjusting means displaces the riser relative to the height of the mounting plate and allows the height of the attachment end to be adjusted in a vertical direction. The riser further includes a means for attachment of an angular adjustment means.

A headrest is hingedly coupled to the attachment end of the riser and movable in an angular direction. The headrest is comprised of a bilobal hoop with a first lobe extending outward and opposite the table and parallel to the top end and a second lobe extending downward and perpendicular to the first lope. The first lobe includes a support strap to support the forehead of the patient. The second lobe is affixed to the angular adjustment means, wherein operation of the adjustment means moves the headrest in an angular direction relative to the table.

In the preferred embodiment, the height adjustment means and angular adjustment means are a pair of adjustable locking gas springs or also known as a gas cylinder. These cylinders are preferably affixed to brackets on the movable parts to provide consistent resistance when making adjustments to the device. Preferably a lever is used to adjust the resistance of the spring wherein the user will activate the lever and move the device to the preferred position. The lever is released and the spring holds the device in position.

BRIEF DESCRIPTION OF THE SEVERAL VIEWS OF THE DRAWING(S)

The accompanying drawings are included to provide a further understanding of the present invention and are incorporated in and constitute a part of this specification. The drawings illustrate exemplary embodiments of the present invention and together with the description serve to further explain the principles of the invention. Other aspects of the invention and the advantages of the invention will be better appreciated as they become better understood by reference to the Detailed Description when considered in conjunction with accompanying drawings, and wherein.

DETAILED DESCRIPTION OF THE INVENTION

Figure 1:
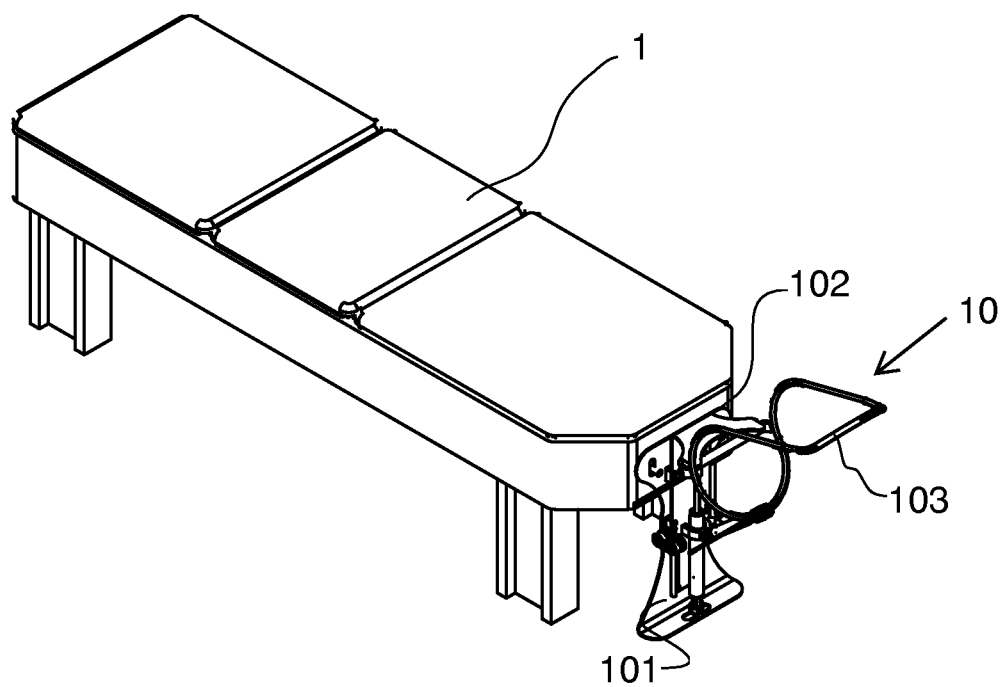
FIG. 1 is an isometric view of the device, according to the present invention.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "front," "back," "rear," "upper," "lower," "right," and "left" in this description are merely used to identify the various elements as they are oriented in the FIGS, with "front," "back," and "rear" being relative to the apparatus. These terms are not meant to limit the elements that they describe, as the various elements may be oriented differently in various applications.

As used herein, the term "coupled" means the joining of two members directly or indirectly to one another. Such joining may be stationary in nature or movable in nature and/or such joining may allow for the flow of fluids, electricity, electrical signals, or other types of signals or communication between two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

Figure 2:
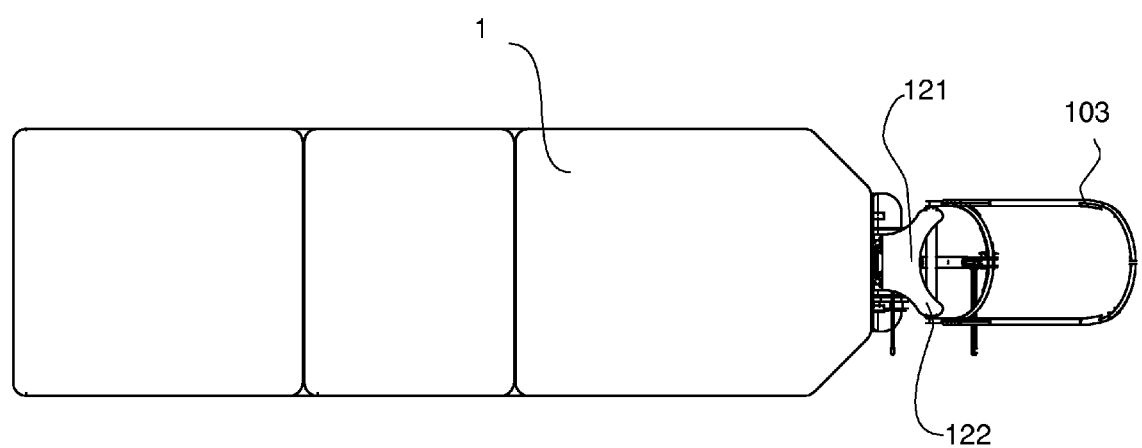
FIG. 2 is a top view of the device, according to the present invention.
Figure 3:
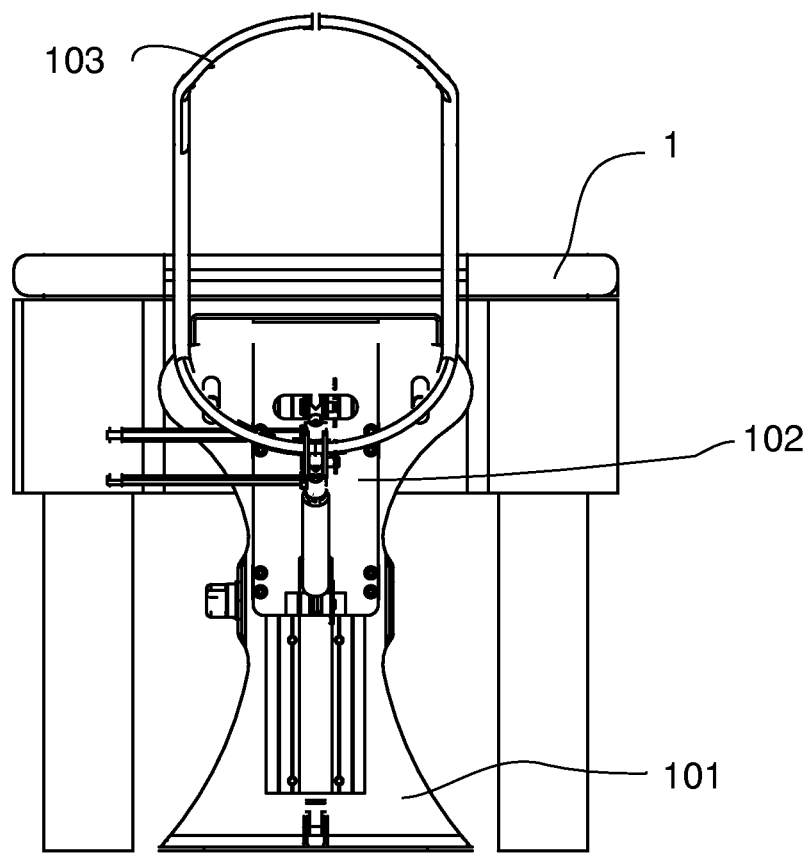
FIG. 3 is a front side view of the device, according to the present invention.
Figure 4:
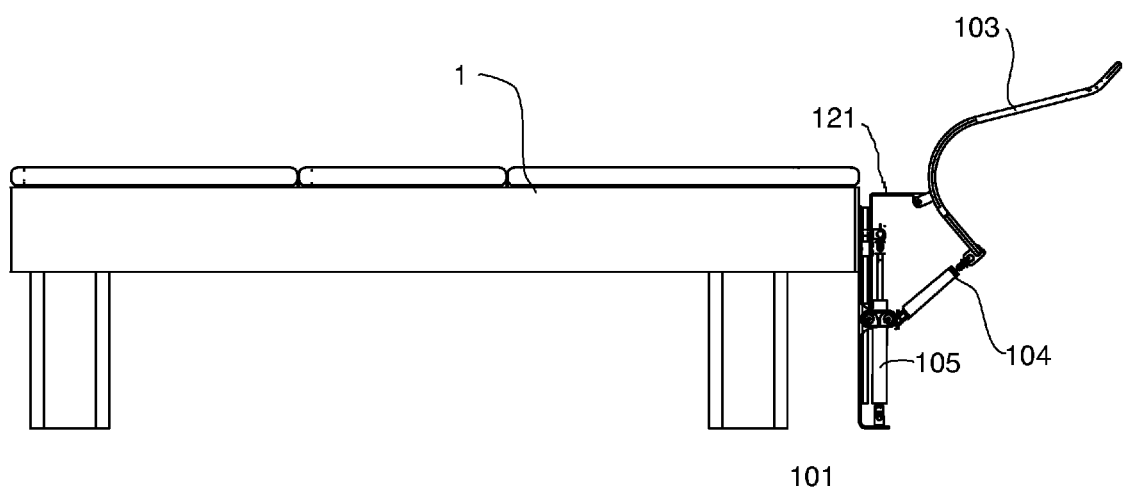
FIG. 4 is a side view of the device, according to the present invention.
Figure 5:
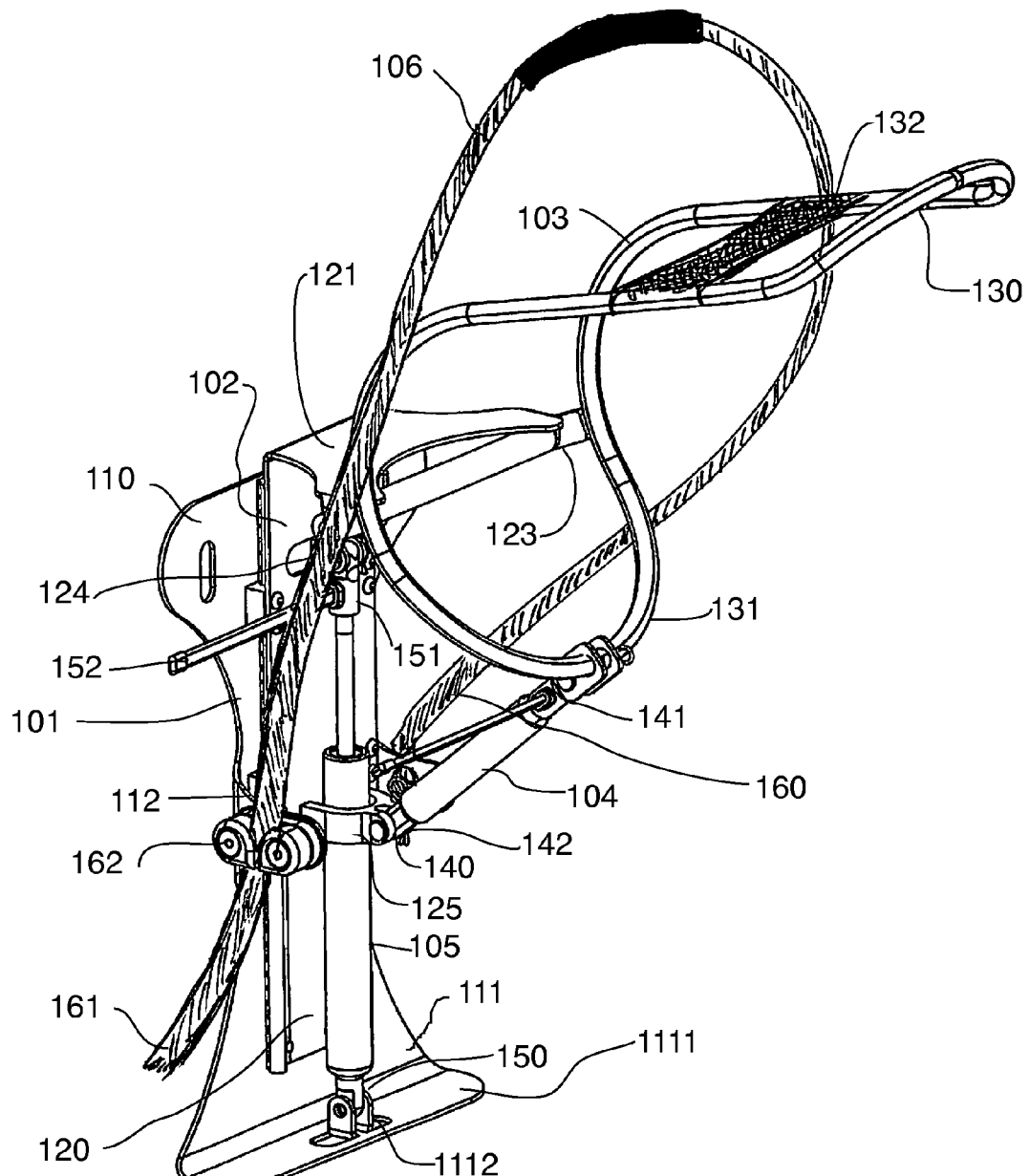
FIG. 5 is a detailed view of the device, according to the present invention.

Referring now to FIGS. 1-5 of a cervical spine fraction device and method for use, the device is generally referred to as 10 and designed to provide traction to the cervical spine of a patient situated within the device 10. The device 10 is affixed to an end of a table 1 and allows for the placement of a patients head onto a support strap 132 while the patient is lying in a prone position. The device 10 is then adjusted to provide the proper angle for treatment and traction is applied to the patient's cervical spine area. The placement and traction position of the device 10 allows for a global head to the ribs downward and forward pull on the cervical spinal unit in lordotic fashion. The device 10 provides the possibility for translation, extension, and compression of the cervical spinal area.

In particular, the device 10 includes a mounting plate 101 having a top end 110 and a bottom end 111 with the distance between the top end 110 and the bottom end 111 extending a height. The mounting plate 101 is attached to an end of the treatment table 1 and aligned with the patient's head when the patient is lying on the table 1 in a prone position. The bottom end 111 includes a foot 1111 for resting on a surface and offering support. The foot 1111 includes a tab 1112, the tab 1112 sized for receipt of a first end 150 of a height adjusting means 105. The mounting plate 101 includes a pair of mounting brackets 112 centrally located on each side of the mounting plate 101, the mounting brackets 112 extending perpendicular to the mounting plate 101 and opposite the table 1.

The mounting brackets 112 are sized and shaped to receive a tensioning means 106 that is designed to provide tension to the neck of the patient. In the preferred embodiment, the tensioning means 106 is a rope having a pair of ends with a first end 160 affixed to one of the pair of mounting brackets 112 that extends around the device and over the patients neck. The rope second end 161 is secured to the second mounting bracket 112 with a cleat 162. Preferably, the cleat 162 is a standard cam action cleat that allows for quick and secure adjustment.

A riser 102 is slidably received along the height of the mounting bracket 101. The riser 102 having a free end 120 and an attachment end 121 opposite the free end 120. The attachment end 121 extends from the riser 102 height and has a bifurcation 122. The bifurcation culminating in a pair of attachment loops 123. The riser 102 includes a pair of tabs 124 to receive a second end 151 of the height adjusting means 105. Wherein adjustment of the height adjusting means 105 displaces the riser 102 relative to the height of the mounting plate 101 and allows the height of the attachment end 121 to be adjusted in a vertical direction. The riser 102 further includes a means for attachment 125 of first end 140 of an angular adjustment means 104.

A headrest 103 is hingedly coupled to the attachment end 122 of the riser 102 and movable in an angular direction. The headrest 103 is comprised of a bilobal hoop with a first lobe 130 extending outward and opposite the table 1 and parallel to the attachment end 122 and a second lobe 131 extending downward and perpendicular to the first lobe lope 130. The first lobe 130 includes a support strap 132 to support the forehead of the patient. The second lobe 131 is affixed to a second end 141 of the angular adjustment means 104, wherein operation of the angular adjustment means 104 moves the headrest 103 in an angular direction relative to the table 1.

In the preferred embodiment, the height adjustment means 105 and angular adjustment means 104 are a pair of adjustable locking gas springs or also known as gas cylinders. These cylinders are preferably affixed to brackets on the movable parts to provide consistent resistance when making adjustments to the device 10. Preferably a lever 152, 142 is used to adjust the resistance of the gas spring, wherein the user will activate the levers and move the device 10 to the preferred position. The lever is released and the spring holds the device in position.

In use, a patient will lie in a prone position on the table 1 and place their forehead onto the strap 132 affixed to the headrest 103. The operator will adjust the height of the device 10 and angle of the device 10 using the height adjustment means 105 and angular adjustment means 104 to the desired position to remodel the patient's cervical spine. The operator will then apply a downward force or traction to the back of the patient's neck using the tensioning means 106. This force is then applied for a set period of time and over several treatment dates to remodel the correct cervical spinal position of the patient.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) but that the invention will include all embodiments falling with the scope of the specification.

What is claimed is:

1. A device for attachment to a treatment table, the device providing support for a patient for the administration of traction to the patient's cervical spinal area, the device comprising:

a mounting plate, the mounting plate affixed to an end of the treatment table, the mounting plate having:
   a top end, the secured to the treatment table;
   a bottom end, the bottom end opposed the top end and defining a height of the mounting plate, the bottom end resting on a surface the treatment table is placed upon, wherein the mounting plate is positioned perpendicular to a length of the treatment table, the bottom end including a tab; and
   a mounting bracket, the mounting bracket positioned on opposed sides of the mounting plate and positioned between the top end and the bottom end;

a riser, the riser slidably received along the mounting plate and movable perpendicular to the length of the treatment table along the height of the mounting plate, the riser having:
   a free end, the free end positioned adjacent to the bottom end of the mounting plate; and
   an attachment end, the attachment end opposite the free end and having an pair of attachment loops and a tab;

a headrest, the headrest in hinged communication with the riser attachment end pair of attachment loops, the headrest comprised of a bilobal hoop having a first lobe and a second lobe, the first lobe extending outward from the attachment and opposite the length of the treatment table, the second lobe extending downward and perpendicular to the first lobe adjacent the attachment end, wherein the headrest is movable in an angular direction relative to a length of the treatment table, the first lobe of the headrest having a strap, the strap allowing for the placement of the patients head;

a height adjustment means, the height adjustment means having a first end and a second end opposite the first end, the first end affixed to the tab of the mounting plate bottom end, the second end affixed to the tab on the riser attachment end, wherein the adjustment of the height adjustment means displaces the riser relative to the height of the mounting plate allowing the height of the riser to be adjusted in a vertical direction;

an angular adjustment means, the angular adjustment means having a first end and a second end opposite the first end, the first end affixed to the riser and the second end affixed to the second lobe of the headrest, wherein the angular adjustment means moves the headrest in an angular direction relative to the length of the table; and a tensioning means, the tensioning means having a first end coupled to the mounting bracket and a length extending around the headrest and adjustable through a coupling on the opposed mounting bracket, wherein the tensioning means provides a traction force to the spine of the patient.

2. The device as in claim 1, wherein the mounting plate bottom end includes a foot, the foot extending perpendicular to the height of the mounting plate and extending opposite the length of the treatment table, the foot providing resting support for the device.

3. The device as in claim 1, wherein the height adjustment means and the angular adjustment means are locking gas springs.

4. The device as in claim 3, wherein the locking gas springs include a lever, the lever capable of adjusting the gas springs to enable the positioning of the device.

5. The device as in claim 1 wherein the mounting bracket includes a cleat, the cleat allowing for adjustment of the tensioning means.

6. The device as in claim 1, wherein the tension means is a rope.

7. The device as in claim 1, wherein the attachment end of the riser includes a bifurcation, the bifurcation culminating in the attachment loops.

8. A method for applying traction to a patients cervical spinal area utilizing the device as in claim 1, the method comprising:
   having the patient lie on a treatment table in a prone position with their head extending off an end of the table;
   supporting their head within the headrest, the headrest adjustable in both a vertical and angular direction;
   moving the head to desired position with the headrest; and
   applying a traction force to the cervical spine of the patient with the tensioning means for a predetermined amount of time.

\* \* \* \* \*